United States Patent [19]

Seitz et al.

[11] Patent Number: 4,564,641

[45] Date of Patent: Jan. 14, 1986

[54] SUBSTITUTED 1-OXO-2-PHENYL-2-(2-ALKYLAMINOE-THYL)-1,2,3,4-TETRAHYDRONAPHTHA-LENES, THEIR PREPARATION AND THEIR USE

[75] Inventors: Werner Seitz, Plankstadt; Hans-Jürgen Teschendorf, Dudenhofen; Alfred Michel, Enkenbach/Alsenborn; Martin Traut, Heidelberg; Hans P. Hofmann, Limburgerhof; Horst Kreiskott, Wachenheim, all of Fed. Rep. of Germany

[73] Assignee: BASF Aktiengesellschaft, Ludwigshafen, Fed. Rep. of Germany

[21] Appl. No.: 554,298

[22] Filed: Nov. 22, 1983

[30] Foreign Application Priority Data

Nov. 25, 1982 [DE] Fed. Rep. of Germany ....... 3243518

[51] Int. Cl.⁴ ................. A61K 31/135; A61K 31/205; C07C 91/16
[52] U.S. Cl. ............................... 514/650; 260/465 F; 260/501.18; 514/319; 514/408; 514/554; 546/206; 548/578; 562/444; 564/304; 564/339
[58] Field of Search ................ 564/339, 304; 424/316, 424/330; 260/501.18; 548/578; 546/206; 514/319, 408, 554, 650

[56] References Cited

U.S. PATENT DOCUMENTS

| | | | |
|---|---|---|---|
| 2,794,048 | 5/1957 | Richter et al. | 564/339 |
| 3,135,799 | 6/1964 | Bencze | 564/308 |
| 3,410,902 | 11/1968 | Draper | 564/339 |
| 3,504,031 | 3/1970 | Berdahl et al. | 564/339 X |
| 3,862,232 | 1/1975 | Lednicer | 564/339 X |

FOREIGN PATENT DOCUMENTS 728103 11/1942 Fed. Rep. of Germany .
1021185 3/1966 United Kingdom .

OTHER PUBLICATIONS

Journal of Medicinal Chemistry, 1977, vol. 20, No. 5, pp. 699–705, "Analgesic and Tranquilizing Activity of 5,8-Disubstituted 1-Tetralone Mannich Bases".

Primary Examiner—Robert V. Hines
Attorney, Agent, or Firm—Oblon, Fisher, Spivak, McClelland & Maier

[57] ABSTRACT

1-Oxo-2-phenyl-2-(2-alkylaminoethyl)-1,2,3,4-tetrahydronaphthalenes of the formula I

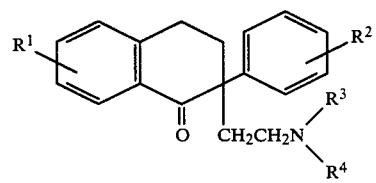

where $R^1$ and $R^2$ are identical or different and are each hydrogen, halogen, trifluoromethyl, $C_1$–$C_4$-alkyl or $C_1$–$C_4$-alkoxy, $R^3$ is $C_1$–$C_6$-alkyl and $R^4$ is hydrogen, $C_1$–$C_6$-alkyl or benzyl, or $R^3$ and $R^4$ together may furthermore be a $C_2$–$C_5$-alkylene chain, and their salts with physiologically tolerated acids, and their preparation, are described.

The novel compounds are useful active compounds for treating disorders.

8 Claims, No Drawings

SUBSTITUTED 1-OXO-2-PHENYL-2-(2-ALKYLAMINOETHYL)-1,2,3,4-TETRAHYDRONAPHTHALENES, THEIR PREPARATION AND THEIR USE

TITLE OF THE INVENTION

1. Field of the Invention

The present invention relates to novel substituted 1-oxo-2-phenyl-2-(2-alkylaminoethyl)-1,2,3,4-tetrahydronaphthalenes, a process for their preparation and their use for treating disorders.

2. Background of the Invention

The tranquilizing, analgesic and neuroleptic actions of substituted 1-oxo-2-dialkylaminomethyl-1,2,3,4-tetrahydronaphthalenes on the central nervous system have been described in a number of publications (eg. J. Med. Chem. 20 (1977), 699 and Naunyn-Schmiedebergs Arch. Exp. Pathol. Pharmakol. 236 (1959), 92, and 238 (1960), 114).

We have found novel compounds which have good antidepressant activity.

SUMMARY OF THE INVENTION

The present invention relates to 1-oxo-2-phenyl-2-(2-alkylaminoethyl)-1,2,3,4-tetrahydronaphthalenes of the formula I

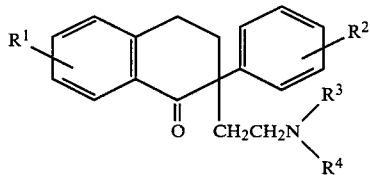

where $R^1$ and $R^2$ are identical or different and are each hydrogen, halogen, trifluoromethyl, $C_1$-$C_4$-alkyl or $C_1$-$C_4$-alkoxy, $R^3$ is $C_1$-$C_6$-alkyl and $R^4$ is hydrogen, $C_1$-$C_6$-alkyl or benzyl, or $R^3$ and $R^4$ together may furthermore be a $C_2$-$C_5$-alkylene chain, and their salts with physiologically tolerated acids.

DESCRIPTION OF THE PREFERRED EMBODIMENTS

Examples of suitable physiologically tolerated acids are hydrochloric acid, hydrobromic acid, sulfuric acid, phosphoric acid, amidosulfonic acid, nitric acid and organic acids, such as acetic acid, propionic acid, oxalic acid, malonic acid, succinic acid, fumaric acid, maleic acid, citric acid, tartaric acid and lactic acid.

$R^1$ and $R^2$ are each preferably hydrogen or chlorine, $R^3$ is preferably methyl and $R^4$ is preferably hydrogen or methyl.

The novel compounds can be prepared by subjecting a 2-phenyl-2-(2-phenethyl)-4-dialkylaminobutanoic acid of the formula II

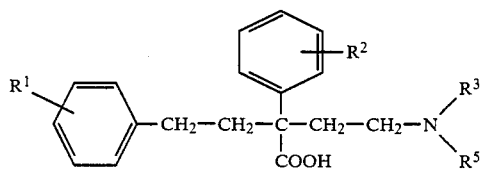

where $R^1$, $R^2$ and $R^3$ have the above meanings and $R^5$ has the same meanings as $R^4$, with the exception of hydrogen, to a cyclization reaction, and, if desired, exchanging the radical $R^5$ in the resulting compound for a hydrogen atom, and, if desired, converting the resulting compound to its salts with physiologically tolerated acids.

The cyclization of the 2-phenyl-2-(2-phenethyl)-4-dialkylaminobutanoic acid II can be carried out by the classical method of Friedel-Crafts acylation. Suitable acylation catalysts include polyphosphoric acid, concentrated sulfuric acid, methanesulfonic acid, mixtures of methanesulfonic acid and phosphorus pentoxide, and hydrofluoric acid. Methanesulfonic acid, or a mixture of this with phosphorus pentoxide, is preferably used.

The reaction temperature for the cyclization reaction depends on the Lewis acid employed, and can vary from 0° to 150° C. The cyclization with methanesulfonic acid is preferably carried out at from 80° to 120° C., while the cyclization using a mixture of methanesulfonic acid with phosphorus pentoxide is preferably carried out at from 20° to 50° C.

The secondary amino compounds of the formula I, where $R^3$ is H and $R^4$ is alkyl, are prepared by a conventional method, by reaction of a tertiary amine of the formula I, where $R^3$ and $R^4$ are each alkyl, with a chloroformate to give a carbamate (formula I), where $R^3$ is alkyl and $R^4$ is COOalkyl, followed by hydrolysis and decarboxylation (M. E. Jung and M. A. Lyster, J. Chem. Soc. Chem. Com. 1978, 315; J. W. Barton in "Protective Groups in Organic Chemistry", edited by J. F. W. McOmie, London 1973, pages 56–61).

The compounds have one or more chiral carbon atoms, for example carbon atom 2 of the 1,2,3,4-tetrahydronaphthalene ring, which atom is substituted by an aryl radical and a dialkylaminoethyl radical. Consequently, the compounds I can be prepared either in the optically active form or as racemic mixtures. If desired, the racemates of the compounds I can be resolved into their optical antipodes by conventional separation techniques, for example by separation (fractional crystallization, column chromatography) of the diastereomeric salts. The latter can be prepared by reacting a compound I with a chiral acid.

Examples of chiral acids are the optically active forms of camphor-10-sulfonic acid, α-bromocamphor-π-sulfonic acid, camphoric acid, menthoxyacetic acid, tartaric acid, mandelic acid and O,O'-diacetyl-, O,O'-dibenzoyl- and O,O'-di-4-toluoyltartaric acid. The separated, pure diastereomeric salts can then be resolved into the optical isomers by a standard method. The racemic compounds I and II can also be resolved into their antipodes by a chromatographic route, using a chiral stationary phase (eg. acetylated crosslinked cellulose).

The 2-phenyl-2-(2-phenethyl)-4-dialkylaminobutanoic acids II not described hitherto can be prepared from the corresponding acid nitriles (III) by hydrolysis of the nitrile group, for example with concentrated hydrobromic acid or with potassium hydroxide in alcohol at elevated temperatures.

The nitriles III can be prepared from the corresponding 2,4-diphenylbutane nitriles by reaction with a 2-dialkylaminoethyl chloride by a process using a phase-transfer catalyst.

The 2,4-diphenylbutane nitriles can be obtained as described in J. Chem. Soc. 1956, page 691.

The optically active forms of the compounds I can be prepared starting from optically active precursors II or III. For this purpose, the compounds II or III are converted to their optically active forms by one of the methods stated above. However, the compounds II can also be separated into their optical antipodes using a chiral base, eg. an α-phenethylamine, brucine, cinchonidine, cinchonine, strychnine, quinine or quinidine.

The novel compounds and their salts with physiologically tolerated acids are useful for the pharmacotherapy of mental disorders, in particular depression.

TEST

The antidepressant action of the substances according to the invention was investigated using the following model:

2.15 mg/kg of reserpine administered subcutaneously to male mice (Swiss strain) weighing 20–26 g lowers the body temperature by an average of 3° C., measured two hours after administration of the reserpine and at an ambient temperature of 20°–22° C. Antidepressants inhibit this hypothermia, the inhibition being dose-dependent. The test substances are administered orally, 60 minutes before the administration of reserpine.

The dose which inhibits the reserpine-induced hypothermia by 50%, ie. the $ED_{50}$, is determined from the linear regression between log dose (mg/kg) and relative decrease in hypothermia.

The results of the test are summarized in Table 1. The $ED_{50}$ values of the compounds according to the invention are predominantly below the $ED_{50}$ determined for the standard antidepressant imipramine, and the substances are therefore more active than the comparative substance. In some cases, the activity is substantially greater than that of imipramine (for Example 18c, by a factor of 72).

TABLE

| Substance of Example No. | Antidepressant action $ED_{50}$ mg/kg, administered orally |
| --- | --- |
| 1 | 0.14 |
| 2 | 6.8 |
| 3 | 4.6 |
| 5 | 4.9 |
| 8 | 5.2 |
| 12 | 0.9 |
| 14 | 2.3 |
| 18a | 0.85 |
| 18c | 0.09 |
| imipramine | 6.8 |

A further feature of the action spectrum of the novel substances is the pronounced inhibition of the reabsorption of biogenic amines, especially norepinephrine and serotonin, in synaptosomes.

The novel compounds can be administered in a conventional manner, either orally or parenterally (subcutaneously, intravenously, intramuscularly or intraperitoneally).

The dosage depends on the age, condition and weight of the patient and on the route of administration. As a rule, the daily dose of active compound is from about 0.01 to 10 mg/kg of body weight for intravenous, subcutaneous or intramuscular administration, as well as for oral administration.

The novel compounds can be used in the conventional solid or liquid pharmaceutical forms for administration, such as tablets, film tablets, capsules, powders, granules, coated tablets, solutions or suppositories. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, slow-release agents and/or antioxidants (cf. H. Sucker et al.: Pharmazeutische Technologie, Thieme-Verlag, Stuttgart 1978). Formulations thus obtained normally contain from 0.1 to 99% by weight of the active compound.

EXAMPLES

The Examples which follow illustrate the invention.

I. PREPARATION OF THE STARTING MATERIALS

A. Nitriles of the acids of the formula II (a) 24 g (0.17 mole) of 2-dimethylaminoethyl chloride hydrochloride were dissolved in 30 ml of water, and 30 ml of 50% strength potassium hydroxide solution were added to the stirred solution. The precipitated base was taken up in 70 ml of toluene, and the solution was dried over anhydrous potassium carbonate and then transferred to a 500 ml three-necked flask. 54 g of 85% pure potassium hydroxide powder, 6 g of potassium carbonate and 0.6 g of tetrabutylammonium iodide were added. A solution of 33.2 g (0.15 mole) of 2,4-diphenylbutane nitrile in 30 ml of toluene was added dropwise to the stirred mixture, the addition being started at room temperature. When the addition was complete, stirring was continued for 2 hours at 80° C.—.

The cold reaction solution was poured into 300 ml of water, and 300 ml of n-hexane were added, after which the organic phase was separated off, washed several times with aqueous sodium chloride solution and dried over potassium carbonate, and the solvent was distilled off. The residue was dissolved in 300 ml of ethyl acetate, and the hydrochloride was precipitated using ethanolic hydrochloric acid. Crystallization from isopropanol gave 37 g (75%) of 2-phenyl-2-(2-phenethyl)-4-dimethylaminobutane nitrile hydrochloride of melting point 214°–216° C.

The following compounds were obtained in a similar manner:

(b) 2-(3-tolyl)-2-(2-phenethyl)-4-dimethylaminobutane nitrile hydrochloride, mp. 208°–210° C., (c) 2-(4-chlorophenyl)-2-(2-phenethyl)-4-dimethylaminobutane, nitrile hydrochloride, mp. 223°–225° C., (d) 2-(4-tolyl)-2-(2-phenethyl)-4-dimethylaminobutane nitrile hydrochloride, mp. 229°–232° C., (e) 2-(4-fluorophenyl)-2-(2-phenethyl)-4-dimethylaminobutane nitrile hydrochloride, mp. 220°–221° C., (f) 2-(2-chlorophenyl)-2-(2-phenethyl)-4-dimethylaminobutane nitrile hydrochloride, mp. 220°–221° C., (g) 2-(3-trifluoromethylphenyl)-2-(2-phenethyl)-4-dimethylaminobutane nitrile hydrochloride, mp. 119°–200° C., (h) 2-(3-chlorophenyl)-2-(2-phenethyl)-4-dimethylaminobutane nitrile hydrochloride, mp. 215°–217° C., (i) 2-phenyl-2-(2-phenethyl)-4-diethylaminobutane nitrile hydrochloride, mp. 208°–210° C., (j) 2-phenyl-2-(2-phenethyl)-4-(pyrrolidin-1-yl)-butane nitrile hydrochloride, mp. 228°–230° C., (k) 2-phenyl-2-(2-phenethyl)-4-(piperidin-1-yl)-butane nitrile hydrochloride, mp. 226°–227° C., (l) 2-phenyl-2-[2-(2-chlorophenyl)ethyl]-4-dimethylaminobutane nitrile, mp. 219°–221° C., (m) 2-phenyl-2-(2-phenethyl)-4-(N-isopropyl-N-benzyl)-aminobutane nitrile, mp. 170°–172° C., (n) 2-(2-fluorophenyl)-2-(2-phenethyl)-4-dimethylaminobutane nitrile hydrochloride, mp. 198°–199° C. and (o) 2-(3-methoxyphenyl)-2-(2-phenethyl)-4-dimethylaminobutane nitrile, mp. 55°–57° C.

B. Acids of the formula II (a) 82.2 g (0.25 mole) of 2-phenyl-2-(2-phenethyl)-4-dimethylaminobutane nitrile hydrochloride were dissolved in 400 ml of 48% strength hydrobromic acid, and the solution was refluxed for 15 hours. The hydrobromic acid was distilled off under reduced pressure, and the residue was then dissolved in 2N NaOH. The solution was extracted several times with ether, and the alkaline solution was then brought to pH 6 with glacial acetic acid. The precipitated acid was filtered off under suction, washed with water and dried to give 70.1 g (90%) of 2-phenyl-2-(2-phenethyl)-4-dimethylaminobutanoic acid. A sample of the acid was recrystallized from a 7:1 mixture of acetonitrile and water, and had a melting point of 223°–225° C. The major part of the acid was used, without further purification, for the cyclization.

The following compounds were obtained in a similar manner:

(b) 2-(3-tolyl)-2-(2-phenethyl)-4-dimethylaminobutanoic acid, (c) 2-(4-chlorophenyl)-2-(2-phenethyl)-4-dimethylaminobutanoic acid, (d) 2-(4-tolyl)-2-(2-phenethyl)-4-dimethylaminobutanoic acid, mp. 195°–196° C., (e) 2-(4-fluorophenyl)-2-(2-phenethyl)-4-dimethylaminobutanoic acid, mp. 218°–220° C., (f) 2-(2-chlorophenyl)-2-(2-phenethyl)-4-dimethylaminobutanoic acid, (g) 2-(3-trifluoromethylphenyl)-2-(2-phenethyl)-4-dimethylaminobutanoic acid, mp. 172°–174° C., (h) 2-(3-chlorophenyl)-2-(2-phenethyl)-4-dimethylaminobutanoic acid, mp. 209°–211° C., (i) 2-phenyl-2-(2-phenethyl)-4-diethylaminobutanoic acid, (j) 2-phenyl-2-(2-phenethyl)-4-(pyrrolidin-1-yl)-butanoic acid, (k) 2-phenyl-2-(2-phenethyl)-4-(piperidin-1-yl)-butanoic acid, (l) 2-phenyl-2-[2-(2-chlorophenyl)-ethyl]-4-dimethylaminobutanoic acid, mp. 176°–179° C., (m) 2-phenyl-2-(2-phenethyl)-4-(N-isopropyl-N-benzyl)-aminobutanoic acid, (n) 2-(2-fluorophenyl)-2-(2-phenethyl)-4-dimethylaminobutanoic acid, mp. 199° C. and (o) 2-(3-methoxyphenyl)-2-(2-phenethyl)-4-dimethylaminobutanoic acid.

II. PREPARATION OF THE END PRODUCTS

EXAMPLE 1

62.3 g (0.2 mole) of 2-phenyl-2-(2-phenethyl)-4-dimethylaminobutanoic acid were dissolved in 200 ml of a mixture of 30 g of phosphorus pentoxide and 350 g of methanesulfonic acid at room temperature, and the stirred solution was kept at 40° C. for 20 hours.

The cold reaction mixture was poured onto ice and rendered alkaline with sodium hydroxide solution, and the base which separated out was extracted with ether. The ether phase was washed several times with sodium chloride solution and dried with magnesium sulfate, and the ether was then distilled off. Recrystallization of the residue from a 1:1 mixture of ether and hexane gave 50 g (85%) of 1-oxo-2-phenyl-2-(2-dimethylaminoethyl)-1,2,3,4-tetrahydronaphthalene of melting point 71°–72° C.

To prepare the hydrochloride, the base was dissolved in ethyl acetate, and the salt was precipitated with ethanolic hydrochloric acid. After recrystallization from ethanol, the hydrochloride had a melting point of 214°–216° C.

The following compounds were obtained by the same procedure:

2. 1-oxo-2-(3-tolyl)-2-(2-dimethylaminoethyl)-1,2,3,4-tetrahydronaphthalene hydrochloride, mp. 232°–234° C., 3. 1-oxo-2-(4-chlorophenyl)-2-(2-dimethylaminoethyl)-1,2,3,4-tetrahydronaphthalene, mp. 113°–115° C., 4. 1-oxo-2-(4-tolyl)-2-(2-dimethylaminoethyl)-1,2,3,4-tetrahydronaphthalene hydrochloride, mp. 239°–243° C., 5. 1-oxo-2-(4-fluorophenyl)-2-(2-dimethylaminoethyl)-1,2,3,4-tetrahydronaphthalene hydrochloride, mp. 270°–273° C., 6. 1-oxo-2-(2-chlorophenyl)-2-(2-dimethylaminoethyl)-1,2,3,4-tetrahydronaphthalene hydrochloride, 7. 1-oxo-2-(3-trifluoromethylphenyl)-2-(2-dimethylaminoethyl)-1,2,3,4-tetrahydronaphthalene hydrochloride, mp. 198°–201° C., 8. 1-oxo-2-(3-chlorophenyl)-2-(2-dimethylaminoethyl)-1,2,3,4-tetrahydronaphthalene hydrochloride, mp. 227°–228° C., 9. 1-oxo-2-phenyl-2-(2-diethylaminoethyl)-1,2,3,4-tetrahydronaphthalene hydrochloride, mp. 218°–220° C., 10. 1-oxo-2-phenyl-2-[2-(pyrrolidin-1-yl)-ethyl]-1,2,3,4-tetrahydronaphthalene hydrochloride, mp. 236°–238° C., 11. 1-oxo-2-phenyl-2-[2-(piperidin-1-yl)-ethyl]-1,2,3,4-tetrahydronaphthalene hydrochloride, mp. 239°–242° C., 12. 1-oxo-5-chloro-2-phenyl-2-(2-dimethylaminoethyl)-1,2,3,4-tetrahydronaphthalene, mp. 107°–109° C., 13. 1-oxo-2-(2-fluorophenyl)-2-(2-dimethylaminoethyl)-1,2,3,4-tetrahydronaphthalene hydrochloride, mp. 179°–180° C. and 14. 1-oxo-2-(3-methoxyphenyl)-2-(2-dimethylaminoethyl)-1,2,3,4-tetrahydronaphthalene hydrogen oxalate, mp. 141°–143° C.

EXAMPLE 15

1-Oxo-2-phenyl-2-(2-methylaminoethyl)-1,2,3,4-tetrahydronaphthalene 29.3 g (0.1 mole) of 1-oxo-2-phenyl-2-(2-dimethylaminoethyl)-1,2,3,4-tetrahydronaphthalene (Example 1) and 16.3 g (0.15 mole) of ethyl chloroformate were dissolved in 200 ml of toluene, and the solution was refluxed for 5 hours. When it had cooled, the toluene solution was washed with 5% strength hydrochloric acid and sodium chloride solution, dried over sodium sulfate and evaporated to dryness.

The residue was dissolved in 100 ml of dry chloroform, and 14 ml (0.1 mole) of trimethylsilyl iodide were added. The mixture was refluxed for 3 hours, after which 100 ml of methanolic hydrochloric acid were added and refluxing was continued for a further 10 minutes. The solvent was distilled off, water was added to the residue, the solution was rendered alkaline with 2N sodium hydroxide solution, and the base which separated out was extracted with ether. The ether solution was washed and dried, and the hydrochloride was precipitated using ethanolic hydrochloric acid, and recrystallized from isopropanol. 22.1 g (70%) of 1-oxo-2-phenyl-2-(2-methylaminoethyl)-1,2,3,4-tetrahydronaphthalene hydrochloride of melting point 152°–154° C. were obtained.

The following compounds were obtained by a similar procedure:
16. 1-oxo-2-phenyl-2-(2-isopropylaminoethyl)-1,2,3,4-tetrahydronaphthalene hydrochloride, mp. 187°–189° C. and
17. 1-oxo-2-phenyl-2-(2-ethylaminoethyl)-1,2,3,4-tetrahydronaphthalene hydrochloride, mp. 183°–185° C.

EXAMPLE 18

Resolution of the racemate of 1-oxo-2-phenyl-2-(2-dimethylaminoethyl)-1,2,3,4-tetrahydronaphthalene (a) Dextrorotatory antipode 29.3 g (0.1 mole) of 1-oxo-2-phenyl-2-(2-dimethylaminoethyl)-1,2,3,4-tetrahydronaphthalene (Example 1) and 20.2 g (0.05 mole) of (−)-O,O′-di-4-toluoyl-L-tartaric acid were dissolved in 400 ml of ethanol. After 5 minutes, the crystals were filtered off under suction, and recrystallized twice from methanol. The angle of rotation found, $[\alpha]_{589}^{20} = +35.8°$ (methanol, c=10 mg/ml), did not change when the substance was recrystallized again. The base liberated from the salt had a melting point of 64°–66° C. and an angle of rotation $[\alpha]_{589}^{20}$ of +249° (methanol, c=10 mg/ml).

The melting point of the hydrochloride was 231°–232° C. and its angle of rotation $[\alpha]_{589}^{20}$ was +238° (methanol, c=10 mg/ml).

(c) Levorotatory antipode

The levorotatory antipode was obtained by reaction with (+)-O,O′-di-4-toluoyl-D-tartaric acid by a procedure similar to that described in (a). Base: mp. 64°–66° C.

$[\alpha]_{589}^{20} = -246°$ (methanol, c=10 mg/ml) Hydrochloride: mp. 231°–232° C.

$[\alpha]_{589}^{20} = -238°$ (methanol, c=10 mg/ml). Pharmaceutical Examples:

EXAMPLE A

A mixture of the following composition was tableted on a tableting press in a conventional manner:
mg of 1-oxo-2-phenyl-2-(2-dimethylaminoethyl)-1,2,3,4-tetrahydronaphthalene hydrochloride, mg of corn starch,
4.5 mg of gelatine,
15 mg of lactose,
7.5 mg of talc,
0.75 mg of Aerosil ® (chemically pure silica in the form of submicroscopic particles) and
2.25 mg of potato starch (as a 6% stength paste).

EXAMPLE B

Coated tablets of the following composition were prepared in a conventional manner:
mg of 1-oxo-2-phenyl-2-(2-dimethylaminoethyl)-1,2,3,4-tetrahydronaphthalene hydrochloride,
mg of core material and
mg of sugar-coating material.

The core material consisted of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consisted of 5 parts of sucrose, 2 parts of corn starch, 2 parts of calcium carbonate and 1 part of talc. The coated tablets thus prepared were then provided with a shell resistant to gastric fluid.

EXAMPLE C 5.0 g of 1-oxo-2-phenyl-2-(2-dimethylaminoethyl)-1,2,3,4-tetrahydronaphthalene hydrochloride were dissovled in 2.0 liters of water, and the solution was made isotonic with sodium chloride and then introduced in a sterile manner into 2 ml ampoules.

We claim:

1. A 1-oxo-2-phenyl-2-(2-aminoethyl)-1,2,3,4-tetrahydronaphthalene of the formula I

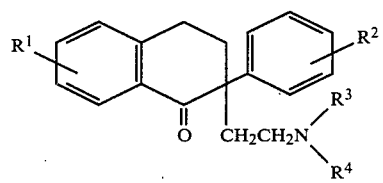

where $R^1$ and $R^2$ are identical or different and are each hydrogen, halogen, trifluoromethyl, $C_1$–$C_4$-alkyl or $C_1$–$C_4$-alkoxy, $R^3$ is $C_1$–$C_6$-alkyl and $R^4$ is hydrogen, $C_1$–$C_6$-alkyl or benzyl, or $R^3$ and $R^4$ together may furthermore be a $C_2$–$C_5$-alkylene chain, and its salts with physiologically tolerated acids.

2. A compound of the formula I as claimed in claim 1, wherein $R^1$ and $R^2$ are each hydrogen and $R^3$ and $R^4$ are each methyl.

3. A compound as claimed in claim 1, in its levorotatory form.

4. A compound of the formula I as claimed in claim 1, wherein $R^1$ and $R^2$ are each hydrogen and $R^3$ and $R^4$ are each methyl, in its levorotatory form.

5. A compound as claimed in claim 1, in its dextrorotatory form.

6. A compound of the formula I as claimed in claim 1, wherein $R^1$ and $R^2$ are each hydrogen and $R^3$ and $R^4$ are each methyl, in its dextrorotatory form.

7. A therapeutic composition comprising a pharmaceutical excipient and an effective amount of a compound as claimed in claim 1.

8. The method of treating mental disorders in a patient suffering therefrom, which comprises administering an effective amount of a compound as claimed in claim 1.

* * * * *